(12) United States Patent
Yamaji (10) Patent No.: US 11,135,109 B2
(45) Date of Patent: Oct. 5, 2021

(54) BED WITH AN ARM AND SENSOR ASSEMBLY

(71) Applicant: FUJITSU LIMITED, Kawasaki (JP)

(72) Inventor: Takayuki Yamaji, Yokohama (JP)

(73) Assignee: FUJITSU LIMITED, Kawasaki (JP)

(*) Notice: Subject to any disclaimer, the term of this patent is extended or adjusted under 35 U.S.C. 154(b) by 276 days.

(21) Appl. No.: 16/000,232

(22) Filed: Jun. 5, 2018

(65) Prior Publication Data

US 2018/0280218 A1    Oct. 4, 2018

Related U.S. Application Data

(63) Continuation of application No. PCT/JP2015/086015, filed on Dec. 24, 2015.

(51) Int. Cl.
| | | |
|---|---|---|
| *A61G 7/015* | (2006.01) | |
| *A61B 5/024* | (2006.01) | |
| *A61B 5/00* | (2006.01) | |
| *A61B 5/0507* | (2021.01) | |
| *A47C 20/04* | (2006.01) | |
| *A61B 5/02* | (2006.01) | |
| *A61B 5/11* | (2006.01) | |

(52) U.S. Cl.
CPC ........... *A61G 7/015* (2013.01); *A47C 20/041* (2013.01); *A47C 20/048* (2013.01); *A61B 5/02444* (2013.01); *A61B 5/0507* (2013.01); *A61B 5/6891* (2013.01); *A61B 5/6892* (2013.01); *A61B 5/02* (2013.01); *A61B 5/11* (2013.01)

(58) Field of Classification Search
CPC .... A61G 7/015; A61B 5/6892; A61B 5/6891; A61B 5/0507; A61B 5/11; A61B 5/68; A61B 5/02444; A61B 5/02; A47C 20/041; A47C 20/048
USPC .......................................................... 5/618
See application file for complete search history.

(56) References Cited

U.S. PATENT DOCUMENTS

| | | | | |
|---|---|---|---|---|
| 3,460,314 A | * | 8/1969 | Keas ..................... | B65B 7/2807 53/72 |
| 3,518,435 A | * | 6/1970 | Kok ......................... | G21K 1/04 378/151 |
| 3,658,133 A | * | 4/1972 | Sweet .................... | A01B 35/16 172/4 |
| 3,772,972 A | * | 11/1973 | Dutro ................... | B65H 29/001 414/788.9 |

(Continued)

FOREIGN PATENT DOCUMENTS

| | | |
|---|---|---|
| JP | 3-264005 | 11/1991 |
| JP | 2004-248808 | 9/2004 |

(Continued)

OTHER PUBLICATIONS

Japanese Office Action dated Nov. 19, 2019 from Japanese Patent Application No. 2017-557586, 11 pages.

(Continued)

*Primary Examiner* — Nicholas F Polito
*Assistant Examiner* — Luke Hall
(74) *Attorney, Agent, or Firm* — Staas & Halsey LLP (57) ABSTRACT

A bed includes a frame installed horizontally with respect to a floor, a plate installed over the frame and having an end portion that is inclined upward with respect to the frame, an arm that supports the plate over the lower side of the plate, and a sensor attached to the arm.

10 Claims, 7 Drawing Sheets

(56) References Cited

U.S. PATENT DOCUMENTS

| | | | | | |
|---|---|---|---|---|---|
| 3,913,729 A | * | 10/1975 | Andrews | | B65G 39/16 198/807 |
| 4,030,353 A | * | 6/1977 | Shutt | | B64D 1/22 73/862 |
| 4,031,752 A | * | 6/1977 | Sanders | | G01B 7/34 73/159 |
| 4,033,492 A | * | 7/1977 | Imai | | B21B 37/50 226/25 |
| 4,158,288 A | * | 6/1979 | Bergstrom | | B21L 19/00 59/1 |
| 4,173,972 A | * | 11/1979 | Kodera | | A61H 7/004 601/102 |
| 4,197,691 A | * | 4/1980 | Woodruff | | A01D 47/00 56/10.2 R |
| 4,230,098 A | * | 10/1980 | Uematsu | | A61H 1/0222 601/115 |
| 4,307,961 A | * | 12/1981 | Blitchington | | G01B 11/272 101/129 |
| 4,315,618 A | * | 2/1982 | Pawlowski | | B23K 7/002 266/69 |
| 4,350,469 A | * | 9/1982 | Corompt | | B60P 1/6463 298/14 |
| 4,357,501 A | * | 11/1982 | Clerc | | B60L 5/16 191/66 |
| 4,403,357 A | * | 9/1983 | Degen | | A47C 17/04 5/618 |
| 4,407,030 A | * | 10/1983 | Elliott | | A61G 7/015 5/424 |
| 4,463,463 A | * | 8/1984 | Kaneko | | A61G 7/015 5/424 |
| 4,637,144 A | * | 1/1987 | Schemel | | B23Q 17/20 33/501.03 |
| 4,656,998 A | * | 4/1987 | Masuda | | A61H 15/0078 601/116 |
| 4,672,184 A | * | 6/1987 | Fujiwara | | G06K 7/10861 235/462.43 |
| 4,686,967 A | * | 8/1987 | Hashimoto | | A61H 1/00 601/116 |
| 4,790,381 A | * | 12/1988 | Armell | | E21B 17/1021 166/241.5 |
| 5,020,518 A | * | 6/1991 | Spears | | A61H 15/0078 601/102 |
| 5,137,016 A | * | 8/1992 | Yamasaki | | A61H 15/0078 601/102 |
| 5,320,641 A | * | 6/1994 | Riddle | | A61H 1/0292 5/618 |
| 5,321,980 A | * | 6/1994 | Hering | | F02D 9/02 123/361 |
| 5,342,036 A | * | 8/1994 | Golicz | | B65H 1/025 271/153 |
| 5,468,216 A | * | 11/1995 | Johnson | | A61H 1/0292 5/616 |
| 5,481,769 A | * | 1/1996 | Schneider | | A47C 20/041 5/424 |
| 5,544,376 A | * | 8/1996 | Fromson | | A61G 7/018 5/618 |
| 5,584,442 A | * | 12/1996 | Watkins | | G03B 17/26 242/348.1 |
| 5,628,078 A | * | 5/1997 | Pennington | | A61B 6/04 5/613 |
| 5,792,080 A | * | 8/1998 | Ookawa | | A61H 1/00 601/102 |
| 6,047,424 A | * | 4/2000 | Osborne | | A61G 7/018 5/600 |
| 6,101,647 A | * | 8/2000 | Stroud | | A47C 20/041 5/613 |
| 6,224,563 B1 | * | 5/2001 | Nonoue | | A61H 15/0078 601/99 |
| 6,276,011 B1 | * | 8/2001 | Antinori | | A47C 20/041 5/613 |
| 6,312,400 B1 | * | 11/2001 | Itikawa | | A61H 7/004 601/100 |
| 6,340,209 B1 | * | 1/2002 | Yamamoto | | B60R 22/26 297/478 |
| 6,393,641 B1 | * | 5/2002 | Hensley | | A47C 20/041 5/613 |
| 6,494,851 B1 | * | 12/2002 | Becher | | A61H 7/001 601/101 |
| 6,606,520 B1 | * | 8/2003 | Lee | | A61F 7/00 601/19 |
| 6,629,939 B2 | * | 10/2003 | Jikiba | | A61H 15/0078 601/100 |
| 6,645,047 B1 | * | 11/2003 | Liskow | | B24B 5/42 451/11 |
| 6,832,991 B1 | * | 12/2004 | Inada | | A61H 39/04 601/100 |
| 7,022,921 B2 | * | 4/2006 | Petrotto | | G01G 19/18 177/144 |
| 7,036,165 B2 | * | 5/2006 | Weinman | | A47C 20/041 5/617 |
| 7,176,391 B2 | * | 2/2007 | Metz | | A61G 7/012 177/144 |
| 7,253,366 B2 | * | 8/2007 | Bhai | | A61B 5/1115 177/144 |
| 7,296,312 B2 | * | 11/2007 | Menkedick | | A61B 5/1115 5/611 |
| 7,335,839 B2 | * | 2/2008 | Metz | | A61G 7/012 177/144 |
| 7,437,787 B2 | * | 10/2008 | Bhai | | A61B 5/1115 177/144 |
| 7,496,457 B2 | * | 2/2009 | Fujita | | A61B 5/1116 702/56 |
| 7,600,817 B2 | * | 10/2009 | Kramer | | A47C 1/022 297/354.13 |
| 7,806,840 B2 | * | 10/2010 | Chen | | A61H 15/0078 601/102 |
| 7,828,756 B2 | * | 11/2010 | Kamba | | A61H 1/003 297/217.3 |
| 7,947,002 B2 | * | 5/2011 | Mizoguchi | | A61H 7/00 601/99 |
| 8,419,300 B2 | * | 4/2013 | Spence | | B41J 15/06 226/24 |
| 8,551,028 B2 | * | 10/2013 | Chen | | A61H 15/0078 601/115 |
| 8,984,686 B2 | * | 3/2015 | Lim | | A61G 7/015 5/613 |
| 9,028,407 B1 | * | 5/2015 | Bennett-Guerrero | | A61B 5/1121 600/301 |
| 9,032,573 B2 | * | 5/2015 | Mijan | | A47C 21/006 5/659 |
| 10,092,480 B2 | * | 10/2018 | Le | | G06F 3/0412 |
| 10,179,084 B2 | * | 1/2019 | Lin | | A61H 7/007 |
| 10,548,806 B2 | * | 2/2020 | Park | | A61H 23/004 |
| 2002/0082612 A1 | * | 6/2002 | Moll | | G09B 23/285 606/130 |
| 2002/0138023 A1 | * | 9/2002 | Kume | | A61H 15/0078 601/99 |
| 2002/0196141 A1 | * | 12/2002 | Boone | | A61G 10/04 340/540 |
| 2003/0061662 A1 | * | 4/2003 | Strobel | | F15B 13/0406 5/618 |
| 2004/0097811 A1 | * | 5/2004 | Smith | | A61B 5/0091 600/448 |
| 2004/0122343 A1 | * | 6/2004 | Mori | | A61H 7/007 601/99 |
| 2004/0158176 A1 | * | 8/2004 | Park | | A61H 39/04 601/18 |
| 2004/0243030 A1 | * | 12/2004 | Tanizawa | | A61H 7/00 601/90 |
| 2005/0103103 A1 | * | 5/2005 | Newman | | G01F 23/54 73/313 |
| 2005/0188462 A1 | * | 9/2005 | Heimbrock | | A61G 7/0507 5/425 |
| 2006/0059624 A1 | * | 3/2006 | Poulos | | A61G 7/002 5/618 |
| 2006/0080777 A1 | * | 4/2006 | Rocher | | A61G 13/08 5/618 |

(56) References Cited

U.S. PATENT DOCUMENTS

| | | | | |
|---|---|---|---|---|
| 2006/0111653 | A1* | 5/2006 | Nishio | A61H 7/001 601/84 |
| 2007/0239089 | A1* | 10/2007 | Chiu | A61H 15/0078 601/99 |
| 2007/0244398 | A1* | 10/2007 | Lo | A61B 8/02 600/500 |
| 2007/0266499 | A1* | 11/2007 | O'Keefe | A61G 7/05784 5/713 |
| 2008/0005838 | A1* | 1/2008 | Wan Fong | A61B 5/4094 5/600 |
| 2008/0009777 | A1* | 1/2008 | Chiu | A61H 15/00 601/99 |
| 2008/0125683 | A1* | 5/2008 | Chen | A61H 15/0078 601/134 |
| 2008/0228062 | A1* | 9/2008 | Zwirn | A61B 5/0046 600/407 |
| 2008/0269629 | A1* | 10/2008 | Reiner | A61B 5/4836 600/544 |
| 2009/0031498 | A1* | 2/2009 | Girard | A61G 7/015 5/617 |
| 2009/0177128 | A1* | 7/2009 | Fukuyama | A61H 15/0078 601/98 |
| 2009/0306558 | A1* | 12/2009 | Chen | 601/101 |
| 2009/0318776 | A1* | 12/2009 | Toda | B60W 40/08 600/301 |
| 2010/0137755 | A1* | 6/2010 | Nagano | A61H 15/00 601/15 |
| 2010/0171622 | A1* | 7/2010 | Brauers | A61G 7/015 340/573.1 |
| 2011/0030141 | A1* | 2/2011 | Soderberg | A61B 5/4839 5/600 |
| 2011/0144453 | A1* | 6/2011 | Kovarik | A61B 10/0038 600/300 |
| 2012/0042451 | A1* | 2/2012 | Jones | A61G 13/0018 5/618 |
| 2012/0116257 | A1* | 5/2012 | Leuthardt | A61B 5/11 600/595 |
| 2012/0151678 | A1* | 6/2012 | Richards | A61G 7/002 5/613 |
| 2013/0047719 | A1* | 2/2013 | Knowles | G01F 23/2962 73/290 V |
| 2014/0135635 | A1* | 5/2014 | Vanderpohl, III | G01G 19/445 600/502 |
| 2015/0018622 | A1* | 1/2015 | Tesar | A61B 50/13 600/202 |
| 2015/0051526 | A1* | 2/2015 | Wang | A61H 15/0078 601/99 |
| 2015/0196442 | A1* | 7/2015 | Heil | A61G 7/005 5/618 |
| 2016/0058639 | A1* | 3/2016 | Lacasse | A61G 7/005 5/610 |
| 2017/0246063 | A1* | 8/2017 | Monson | A61B 5/6808 |
| 2018/0184887 | A1* | 7/2018 | Abou El Kheir | A61B 1/313 |

FOREIGN PATENT DOCUMENTS

| | | | | |
|---|---|---|---|---|
| JP | 2008-113946 | | 5/2008 | |
| JP | 2008-131974 | | 6/2008 | |
| JP | 2011-15971 | | 1/2011 | |
| JP | 2011-110068 | | 6/2011 | |
| JP | 2011110068 A | * | 6/2011 | ............ A61B 5/11 |
| JP | 2011110068 A | * | 6/2011 | |
| JP | 2014-97385 | | 5/2014 | |
| JP | 2014-210137 | | 11/2014 | |

OTHER PUBLICATIONS

International Search Report dated Mar. 15, 2016 in corresponding International Patent Application No. PCT/JP2015/086015.
Written Opinion of the International Searching Authority dated Mar. 15, 2016 in corresponding International Patent Application No. PCT/JP2015/086015.
Japanese Office Action dated Jun. 4, 2019 from Japanese Patent Application No. 2017-557586, 11 pages.

* cited by examiner

BED WITH AN ARM AND SENSOR ASSEMBLY

CROSS-REFERENCE TO RELATED APPLICATION

This application is a continuation application of International Application PCT/JP2015/086015 filed on Dec. 24, 2015 and designated the U.S., the entire contents of which are incorporated herein by reference.

FIELD

The embodiments discussed herein are related to a bed having a back lifting mechanism.

BACKGROUND

A technique for causing a sensor installed in a mattress of a bed or in a bed to detect the state (for example, pulse, breathing, body motion, and the like) of a sleeping user is known.

However, since the aforementioned conventional technique focuses on only the sensing of the state (supine state) of a sleeping user, it is difficult to apply the conventional technique to a bed having a back lifting mechanism.

The followings are reference documents:
[Document 1] Japanese Laid-open Patent Publication No. 2008-113946 and
[Document 2] Japanese Laid-open Patent Publication No. 2014-210137.

SUMMARY

According to an aspect of the invention, a bed includes a frame installed horizontally with respect to a floor, a plate installed over the frame and having an end portion that is inclined upward with respect to the frame, an arm that supports the plate over the lower side of the plate, and a sensor attached to the arm.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Hereinafter, embodiments are described with reference to the accompanying drawings.

Figure 1A:
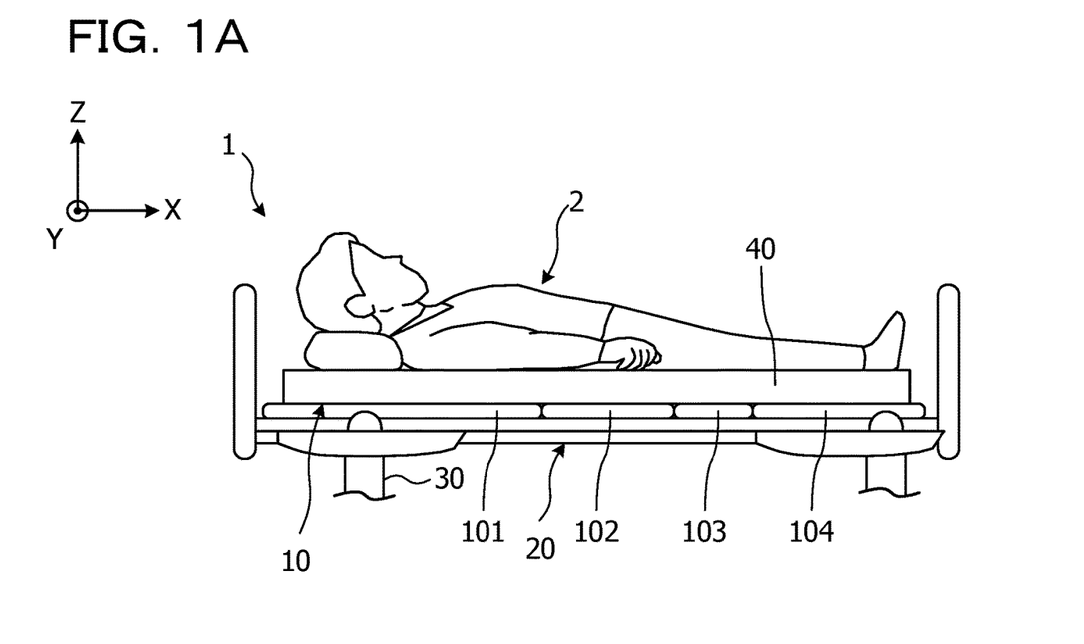
FIG. 1A is a diagram schematically illustrating a non-back-lifted state.
Figure 1B:
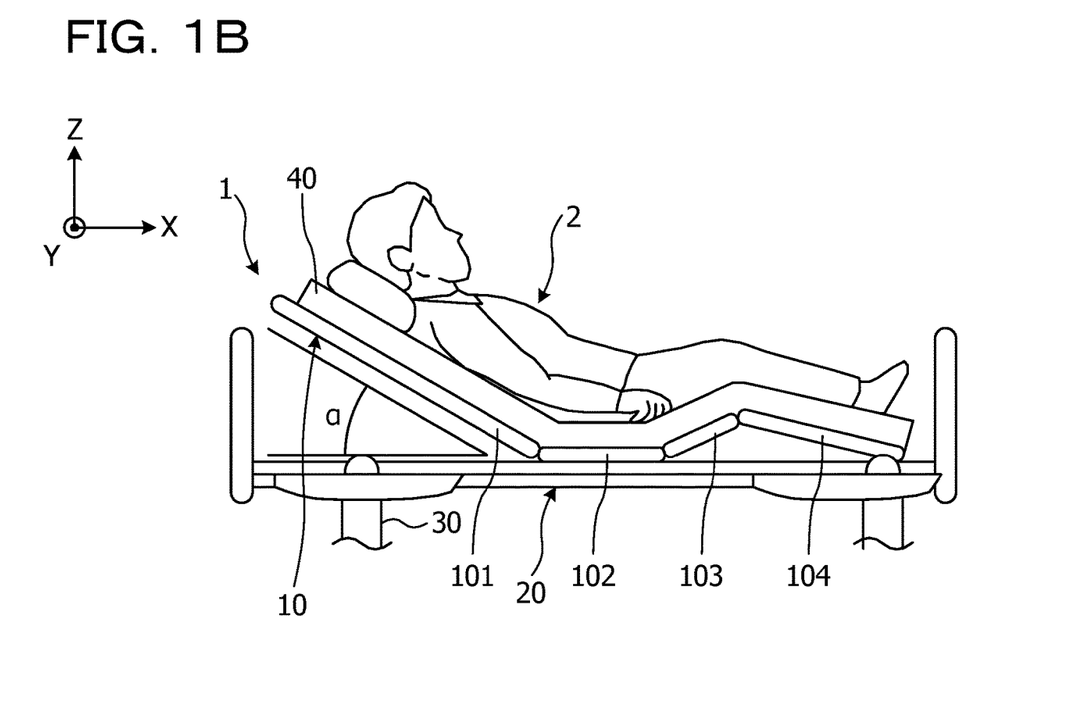
FIG. 1B is a diagram schematically illustrating a back-lifted state.

FIGS. 1A and 1B are diagrams describing a back lifting mechanism of a bed 1 according to an embodiment. FIG. 1A is the diagram schematically illustrating a non-back-lifted state, while FIG. 1B is the diagram schematically illustrating a back-lifted state. FIGS. 1A and 1B illustrate a user 2 lying on the bed 1. Since FIGS. 1A and 1B are the simplified diagrams, FIGS. 1A and 1B do not illustrate a detailed structure of the back lifting mechanism and the like.

The bed 1 is, for example, a nursing bed and has the back lifting mechanism. The back lifting mechanism lifts up the back of the user 2 lying on the bed 1 against the lower body of the user 2. The back lifting mechanism changes the state of a back portion 10 of the bed 1 from a non-back-lifted state in which the back portion 10 extends on a horizontal plane to a back-lifted state in which the back portion 10 forms an angle larger than 0 degrees with respect to the horizontal plane, and the back lifting mechanism is able to maintain the back-lifted state. Hereinafter, an angle "a" (refer to FIG. 1B) of the back portion 10 of the bed 1 with respect to the horizontal plane (floor surface) is referred to as "back lifting angle". The back lifting mechanism may adjust the back lifting angle in multiple stages or in a stepless manner or may adjust the back lifting angle in only a single stage (or switches the state of the back portion 10 between the two states or between the back-lifted state and the non-back-lifted state).

Figure 2:
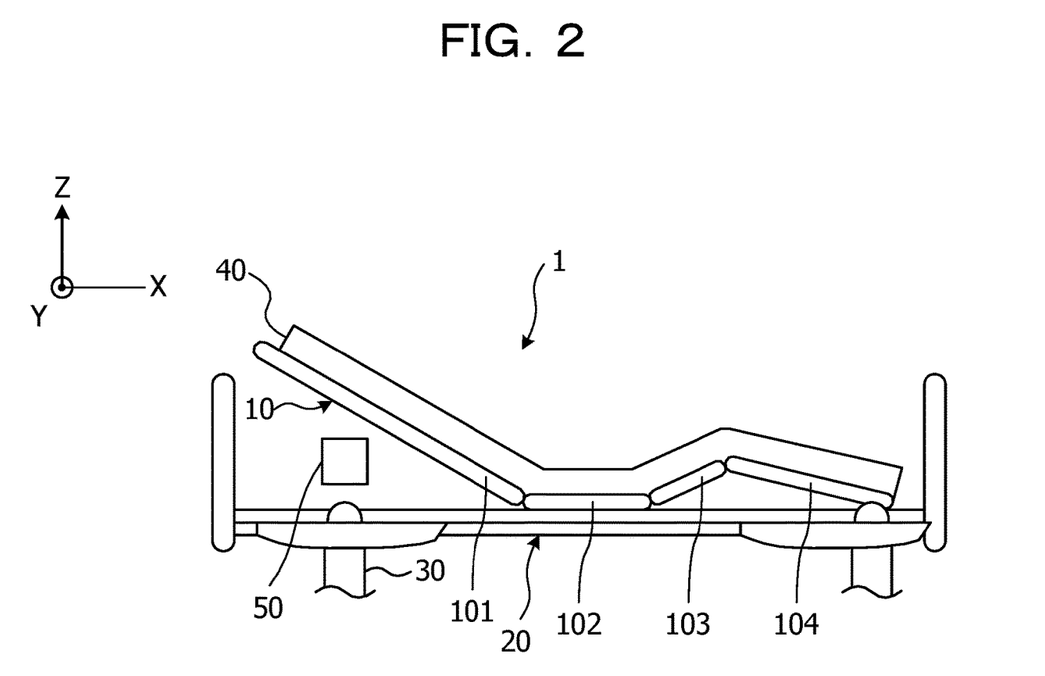
FIG. 2 is a simplified explanatory diagram of the structure of a bed.

FIG. 2 is a simplified explanatory diagram of the structure of the bed 1. Since FIG. 2 is the simplified explanatory diagram, FIG. 2 does not illustrate a detailed structure. FIG. 2 illustrates the back lifting mechanism 50 in a conceptually simplified manner. Three axes X, Y, and Z are illustrated in FIG. 2 and perpendicular to each other are used for the following description. The Y direction corresponds to a width direction of the bed 1.

The bed 1 includes the back portion 10, a frame portion 20, a leg portion 30, a mattress 40, and the back lifting mechanism 50, as illustrated in FIG. 2. The frame portion 20 is substantially horizontal to a floor.

The back portion 10 includes a back bottom 101 for supporting the back of the user 1 via the mattress 40. In an example illustrated in FIG. 2, the back bottom 101 is composed of a single bottom portion but may include multiple back bottom portions coupled to each other so that the multiple back bottom portions are relatively rotatable about the Y axis. The back bottom 101 may include a mesh metal portion extending on a flat surface, for example. In the following description, the flat surface of the back bottom 101 is a basic surface of the back bottom 101 and is a horizontal surface in the non-back-lifted state.

The back bottom 101 is coupled to a buttock bottom 102 for supporting buttocks of the user 2 so that the buttock bottom 102 is relatively rotatable about the Y axis. Alternatively, the back bottom 101 may not be coupled to the buttock bottom 102 (refer to a second embodiment described later). Similarly, the buttock bottom 102 is coupled to a thigh bottom 103 for supporting thighs of the user 2 so that the thigh bottom 103 is relatively rotatable about the Y axis. The thigh bottom 103 is coupled to a lower leg bottom 104 for supporting lower legs of the user 2 so that the lower leg bottom 104 is relatively rotatable about the Y axis.

The frame portion 20 includes a metal frame member, for example. The frame portion 20 may have a lattice structure and include multiple frame members extending in the X direction and multiple frame members extending in the Y direction. The frame portion 20 has a function of supporting the back portion 10, the back lifting mechanism 50 described later, and the like.

The leg portion 30 supports the frame portion 20 against the floor. The leg portion 30 enables a simple movement of the bed 1 and may include wheels at lower ends of the leg portion 30.

The mattress 40 has flexibility (or bends along the Y axis) or is able to be deformed to some extent, depending on the back lifting angle. Alternatively, the mattress 40 may include multiple members corresponding to the back bottom 101, the buttock bottom 102, the thigh bottom 103, and the lower leg bottom 104 and coupled to each other so that the multiple members are relatively rotatable about the Y axis (or able to bend). A lower surface of the mattress 40 is in contact with an upper surface of the back bottom 101, an upper surface of the buttock bottom 102, an upper surface of the thigh bottom 103, and an upper surface of the lower leg bottom 104. The back bottom 101, the buttock bottom 102, the thigh bottom 103, and the lower leg bottom 104 support the entire lower surface of the mattress 40 while collaborating with each other. Specifically, the back bottom 101, the buttock bottom 102, the thigh bottom 103, and the lower leg bottom 104 form a mattress supporting portion that is in contact with the mattress 40.

The back lifting mechanism 50 is a mechanism unit that achieves the aforementioned back lifting function. The back lifting mechanism 50 may be electrically, hydraulically, or manually operated. The following assumes that the back lifting mechanism 50 is electrically operated. In other words, it is assumed that the back lifting mechanism 50 is electrically operated to achieve the aforementioned back lifting function.

The back lifting mechanism 50 may have an arbitrary configuration as long as the back lifting mechanism 50 achieves the aforementioned back lifting function. The back lifting mechanism 50 may have a lumbar support function, for example.

Next, embodiments that are related to a sensor attachment structure that may be included in the aforementioned bed 1 are described.

First Embodiment

Figure 3:
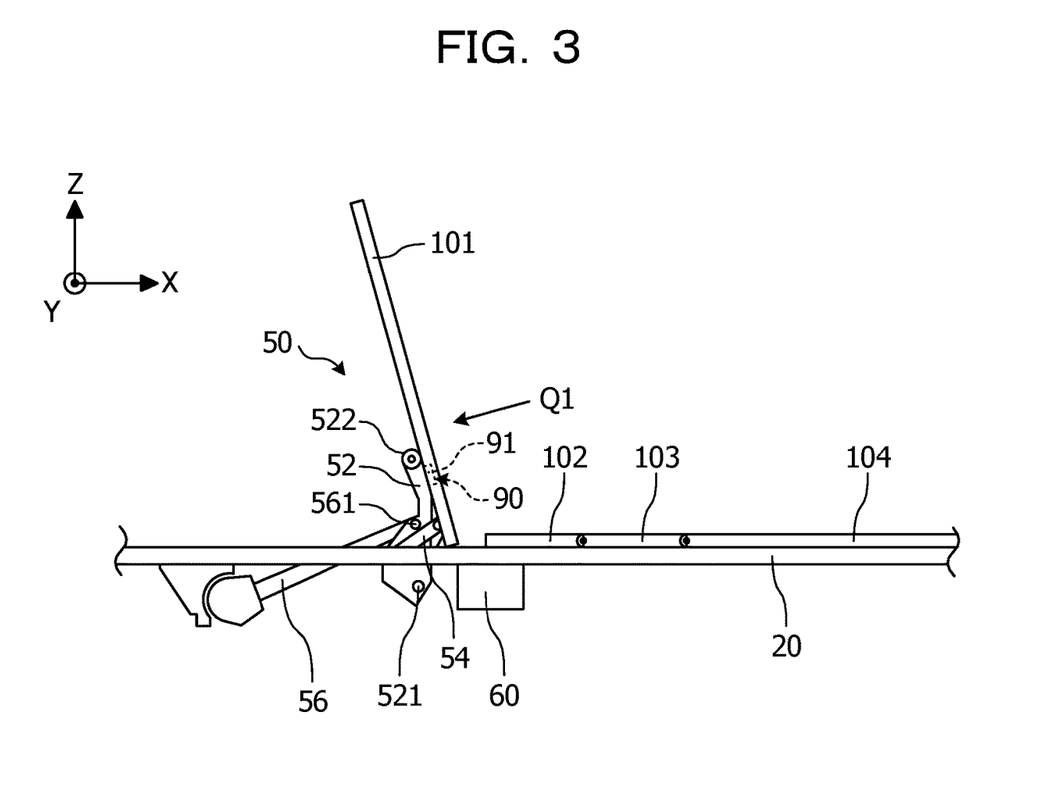
FIG. 3 is a simplified diagram illustrating an example of a back lifting mechanism of the bed according to an embodiment.
Figure 4:
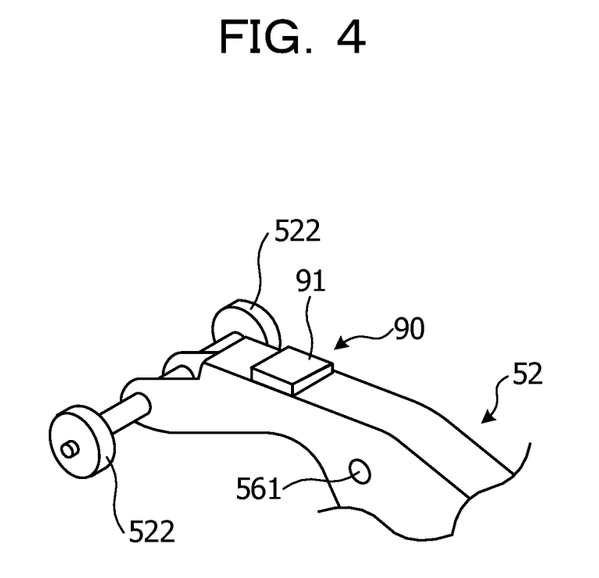
FIG. 4 is a perspective view illustrating an example of a state in which a sensor unit is attached.

FIG. 3 is a simplified diagram illustrating an example of the back lifting mechanism 50 of the bed 1. Since FIG. 3 is the simplified diagram, FIG. 3 does not illustrate a detailed structure. For example, FIG. 3 illustrates an electric motor 56 in a conceptually simplified manner. In addition, FIG. 3 illustrates the back lifting mechanism 50 in the back-lifted state. FIG. 4 is a perspective view illustrating an example of a state in which a sensor unit 90 is attached.

The back lifting mechanism 50 includes a back lifting arm 52, a back lifting driven arm 54, and the electric motor 56.

A lower end of the back lifting arm 52 is supported by the frame portion 20 so that the lower end of the back lifting arm 52 is rotatable about the Y axis by a rotational pivot 521. Rollers 522 of an upper end of the back lifting arm 52 slidably support the back bottom 101. When the back lifting arm 52 is driven and rotated about the rotational pivot 521 in a clockwise direction in FIG. 3, the back lifting arm 52 lifts up the back bottom 101 while the rollers 522 slide on a lower surface of the back bottom 101.

Similarly, a lower end of the back lifting driven arm 54 is supported by the frame portion 20 so that the lower end of the back lifting driven arm 54 is rotatable about the Y axis by the rotational pivot 521. An upper end of the back lifting driven arm 54 is supported by the back bottom 101 so that the upper end of the back lifting driven arm 54 is rotatable about the Y axis.

The electric motor 56 generates driving force to drive the back lifting arm 52 and rotate the back lifting arm 52 about the rotational pivot 521 and about the Y axis. The electric motor 56 is electrically connected to a power unit 60. For example, the electric motor 56 is electrically connected to the power unit 60 via a cord or a harness (not illustrated). The power unit 60 is fixed to the frame portion 20, for example. The power unit 60 may be electrically connected to an external alternating-current source (for example, alternating-current source for home use). In this case, the power unit 60 generates power to drive the electric motor 56 and the like based on the external alternating-current source. The power unit 60 may include a battery that is charged by power from the external alternating-current source. In this case, the electric motor 56 may operate based on power from the battery.

In the example illustrated in FIG. 3, the electric motor 56 electrically expands and contracts a cylinder rod, thereby driving the back lifting arm 52 and rotating the back lifting arm 52 about the rotational pivot 521 and about the Y axis. An upper end of the cylinder rod is supported by the back lifting arm 52 so that the upper end of the cylinder rod is rotatable about a rotational pivot 561 and about the Y axis.

In a first embodiment, the bed 1 includes the sensor unit 90 (that is an example of a sensor). The sensor unit 90 includes a biological sensor that detects the state of the user 2 lying on the bed 1. The biological sensor may include a sensor that emits a radio wave (for example, microwave) and acquires biological information (information indicating an activity, breathing, a heart rate, and the like of the user 2 or the like) based on a reflected wave of the radio wave. In this case, the sensor unit 90 may be used in a system that monitors the user 2 (for example, a specific person such as an ill person or an elderly person) lying on the bed 1. Hereinafter, as an example, it is assumed that the sensor unit 90 includes only the biological sensor that emits a radio wave and acquires biological information based on a reflected wave of the radio wave. The sensor unit 90, however, may include another sensor other than the biological sensor.

The sensor unit 90 has directionality. In this case, as an example, it is assumed that the directionality is maximized in a normal direction (orientation) of a sensing surface 91 and the sensor unit 90 has a sensing range whose center is the normal direction of the sensing surface 91. In the following description, a sensing direction of the sensor unit 90 indicates the normal direction of the sensing surface 91.

In the example illustrated in FIGS. 3 and 4, the sensor unit 90 is attached to an upper surface of the back lifting arm 52. In this case, the sensor unit 90 is attached to the back lifting arm 52 so that the sensing direction passes through a predetermined region (hereinafter referred to as "heart sensing-enabled region") fixedly located with respect to the back bottom 101 in a state in which the back lifting angle is any value in a changeable range of the back lifting angle. The heart sensing-enabled region is set to a range in which the chest or heart of the user 2 lying on the bed 1 may be located when viewed in a direction perpendicular to the flat surface of the back bottom 101 (refer to FIG. 5). In this case, the sensing direction of the sensor unit 90 is likely to be oriented toward the heart of the user 2. If the sensing direction of the sensor unit 90 is oriented toward the heart of the user 2, the accuracy of the detection by the sensor unit 90 may be high. A position and angle at which the sensor unit 90 is attached to the back lifting arm 52 may be individually set based on the size of the body of the user 2 and the like.

A method for attaching the sensor unit 90 to the back lifting arm 52 is arbitrary. For example, the sensor unit 90 may be attached to the back lifting arm 52 using a fastener such as a bolt or a screw. Alternatively, the sensor unit 90 may be attached to the back lifting arm 52 using an adhesive, a tape, or the like. Alternatively, the sensor unit 90 may be attached directly to the back lifting arm 52 as schematically illustrated in FIG. 3 or may be attached to the back lifting arm 52 via a stay or a bracket.

The sensor unit 90 may operate with an internal battery. It is preferable that the sensor unit 90 operate based on power from an external power unit. It is preferable that the external power unit be the power unit 60 that supplies power to the electric motor 56. In this case, since the existing power unit 60 is used, the sensor unit 90 is operated without a dedicated power unit. In the example illustrated in FIG. 3, the sensor unit 90 is electrically connected to the power unit 60 via a cord or a harness (not illustrated). Since the sensor unit 90 is located at a position related to the back lifting mechanism 50 and may be installed relatively close to the electric motor 56, it is easy to wire the cord or the harness.

Figure 5:
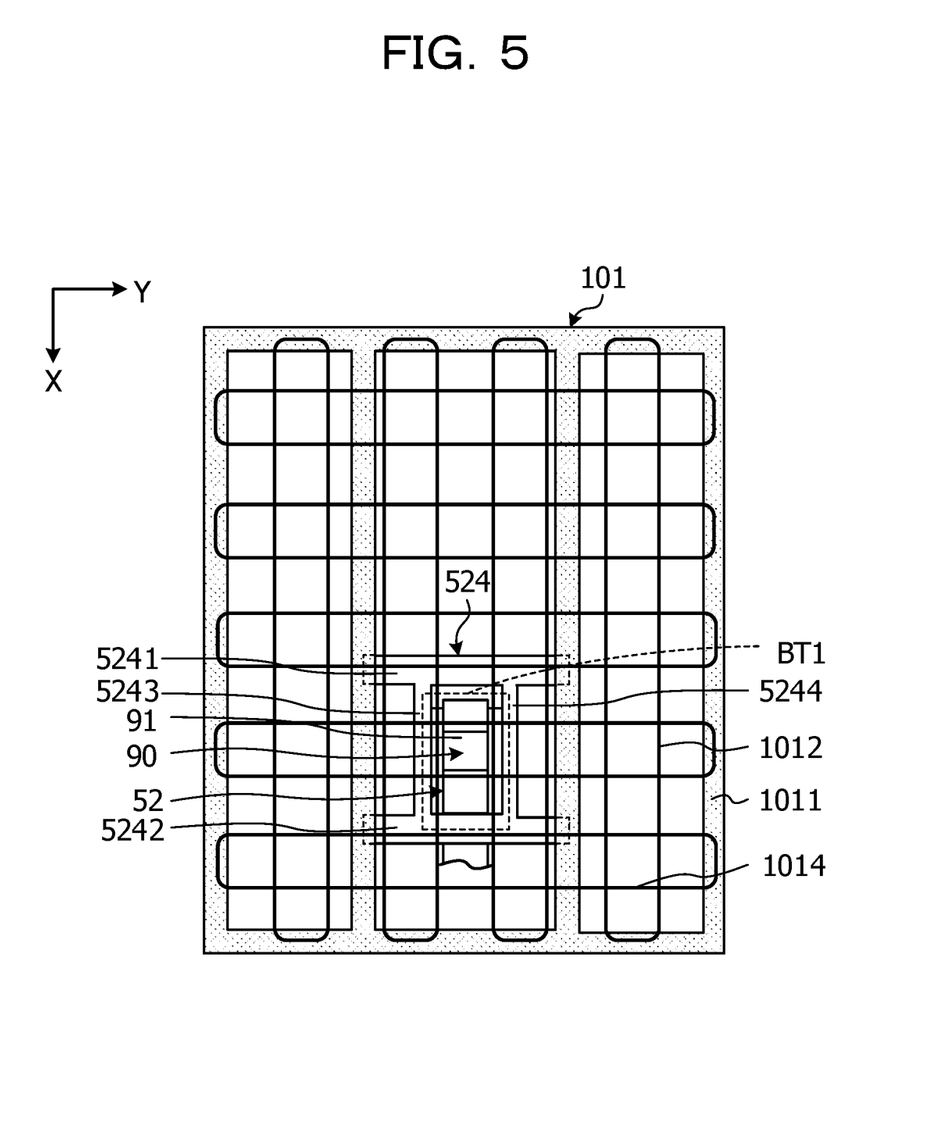
FIG. 5 is a diagram schematically illustrating an example of the state in which the sensor unit is attached when viewed in a direction indicated by an arrow Q1 in FIG. 3.

FIG. 5 is a diagram schematically illustrating an example of a state in which the sensor unit is attached when viewed in a direction indicated by an arrow Q1 in FIG. 3. The direction indicated by the arrows Q1 corresponds to the direction perpendicular to the flat surface of the back bottom 101. FIG. 5 illustrates the back bottom 101, the back lifting arm 52, and the sensor unit 90. In addition, FIG. 5 illustrates the heart sensing-enabled region BT1. In the example illustrated in FIG. 5, the heart sensing-enabled region BT1 is set to a central portion in the width direction (Y direction) of the bed 1.

In the example illustrated in FIG. 5, the back bottom 101 includes a body portion 1011 that is a structural member of the lattice structure, vertical mesh portions 1012 forming mesh stripe portions extending in the vertical direction, and vertical mesh portions 1014 forming mesh stripe portions extending in the horizontal direction. In FIG. 5, only the body portion 1011 is hatched for clarity in a formal manner. The vertical mesh portions 1012 and the vertical mesh portions 1014 are welded together with the body portion 1011, for example. The vertical mesh portions 1012 and the vertical mesh portions 1014 are welded at positions where the vertical mesh portions 1012 and the vertical mesh portions 1014 intersect with each other. In the example illustrated in FIG. 5, the back bottom 101 includes a roller support structure 524 that supports the rollers 522 of the back lifting arm 52. The roller support structure 524 includes two horizontal frame portions 5241 and 5242 and two vertical frame portions 5243 and 5244. The rollers 522 are in contact with lower surfaces of the vertical frame portions 5243 and 5244 so that the rollers 522 are slidable on the lower surfaces of the vertical frame portions 5243 and 5244.

The back lifting arm 52 is located on the side (side opposite to the side on which the back bottom 101 is in contact with the mattress 40) of the lower surface of the back bottom 101. The horizontal frame portions 5241 and 5242 extend in the Y direction, while there is a gap between the horizontal frame portions 5241 and 5242 in the X direction.

The vertical frame portions 5243 and 5244 extend in the X direction, while there is a gap between the vertical frame portions 5243 and 5244 in the Y direction. In the example illustrated in FIG. 5, when viewed in the direction perpendicular to the flat surface of the back bottom 101, the heart sensing-enabled region BT1 includes a region between the horizontal frame portions 5241 and 5242 and a region between the vertical frame portions 5243 and 5244. The sensor unit 90 is installed so that the sensing direction passes through the region between the horizontal frame portions 5241 and 5242 and the region between the vertical frame portions 5243 and 5244 in a state in which the back lifting angle is any value in the changeable range of the back lifting angle. Thus, the sensing direction of the sensor unit 90 may pass through the heart sensing-enabled region BT1 in a state in which the back lifting angle is any value in the changeable range of the back lifting angle. The sensor unit 90 may be attached to the back bottom 101 so that the sensing direction corresponds to the direction perpendicular to the flat surface of the back bottom 101.

In a comparative example (not illustrated) in which the sensor unit 90 is installed in the mattress 40, the mattress 40 may be deformed upon an operation (for example, operation upon the transition from the non-back-lifted state to the back-lifted state or from the back-lifted state to the non-back-lifted state) of the back lifting mechanism 50. In addition, the mattress 40 may be deformed with respect to the back bottom 101 upon the operation of the back lifting mechanism 50. Thus, in the comparative example, a relatively large load is applied to the sensor unit 90 for each operation of the back lifting mechanism 50, and the sensor unit 90 may be detached or the position of the sensor unit 90 may be shifted.

On the other hand, according to the first embodiment, as described above, the sensor unit 90 is not installed in the mattress 40 and is attached to the back lifting arm 52 that is a supporting member that supports the back portion 10. Thus, according to the first embodiment, a load caused by the operation of the back lifting mechanism 50 is not applied to the sensor unit 90, and the aforementioned inconvenience caused in the comparative example may be reduced.

In addition, according to the first embodiment, as described above, since the sensor unit 90 is installed on the lower side of the back bottom 101, the sensor unit 90 is more reliably attached than the case where the sensor unit 90 is installed between the mattress 40 and the back bottom 101. Specifically, if the sensor unit 90 is installed on the upper surface of the back bottom 101 and the mattress 40 is shifted with respect to the back bottom 101 due to the transition from the non-back-lifted state to the back-lifted state, shear stress may occur in an attached portion of the sensor unit 90. As a result, the attached portion of the sensor unit 90 may be easily fractured. On the other hand, in the first embodiment, the sensor unit 90 is not in contact with the mattress 40, inconvenience caused by a shift (displacement) of the mattress 40 with respect to the back bottom 101 does not occur.

In addition, in the first embodiment, as described above, the sensor unit 90 is attached to the upper surface of the back lifting arm 52 so that the sensing direction passes through the heart sensing-enabled region BT1 in a state in which the back lifting angle is any value in the changeable range of the back lifting angle. Thus, according to the first embodiment, the sensor unit 90 is likely to accurately detect the state of the user 2 in the non-back-lifted state and the back-lifted state. As a result, not only during the time when the user 2 is lying on the bed 1 but also during the time when the user 2 is sitting on the bed 1 in the back-lifted state, the state of the user 2 may be accurately detected by the sensor unit 90.

Especially, in a state in which the back lifting angle is any value in the changeable range of the back lifting angle, the upper surface of the back lifting arm 52 maintains a certain angle with respect to the flat surface of the back bottom 101. Thus, in a state in which the back lifting angle is any value in the changeable range of the back lifting angle, the sensing direction of the sensor unit 90 maintains a certain angle with respect to the flat surface of the back bottom 101. In addition, a relative position of the sensor unit 90 on the upper surface of the back lifting arm 52 with respect to the back bottom 101 only slightly changes depending on the back lifting angle. Thus, in the first embodiment, in the non-back-lifted state and the back-lifted state, the state of the user 2 is likely to be accurately detected by the sensor unit 90.

In addition, in the first embodiment, the back lifting arm 52 is not a dedicated member to be used to attach the sensor unit 90 and may be an existing member. Thus, according to the first embodiment, the sensor unit 90 may be attached at an appropriate position while the number of members does not increase.

Second Embodiment

Figure 6:
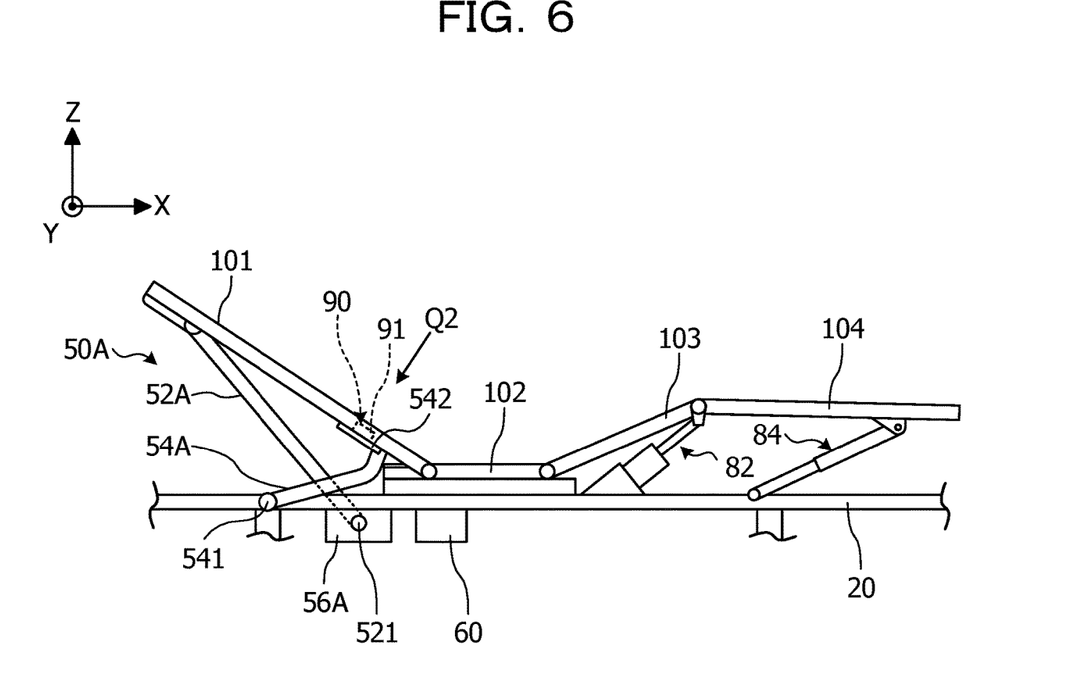
FIG. 6 is a simplified diagram illustrating an example of a back lifting mechanism of a bed according to a second embodiment.

FIG. 6 is a simplified diagram illustrating an example of a back lifting mechanism 50A of a bed 1. Since FIG. 6 is the simplified diagram, FIG. 6 does not illustrate a detailed structure. For example, FIG. 6 illustrates an electric motor 56A in a conceptually simplified manner. FIG. 6 schematically illustrates the back lifting mechanism 50A, a mechanism unit 82 for lifting up a rotational pivot located between the thigh bottom 103 and the lower leg bottom 104, and a mechanism unit 84 for lifting up a free end of the lower leg bottom 104.

In the following description of the second embodiment, constituent elements that may be the same as or similar to those described in the first embodiment are indicated by the same reference symbols as those described in the first embodiment, and a description thereof is simplified or omitted.

The back lifting mechanism 50A includes a back lifting arm 52A, a back lifting driven arm 54A, and the electric motor 56A.

A lower end of the back lifting arm 52A is supported by the frame portion 20 so that the lower end of the back lifting arm 52A is rotatable about the Y axis by the rotational pivot 521. Rollers of an upper end of the back lifting arm 52A slidably support the back bottom 101A. When the back lifting arm 52A is driven and rotated about the Y axis in a clockwise direction in FIG. 6, the back lifting arm 52A lifts up the back bottom 101A while the rollers of the back lifting arm 52A slide on a lower surface of the back bottom 101A.

A lower end of the back lifting driven arm 54A is supported by the frame portion 20 so that the lower end of the back lifting driven arm 54A is rotated about the Y axis by the rotational pivot 541. An upper end of the back lifting driven arm 54A is supported by the back bottom 101A so that the upper end of the back lifting driven arm 54A is rotatable. In the example illustrated in FIG. 6, the upper end of the back lifting driven arm 54A is supported by an arm pivot member 542 so that the upper end of the back lifting driven arm 54A is rotatable. The arm pivot member 542 is fixed on the side of the lower surface of the back bottom 101A. The upper end of the back lifting driven arm 54A is supported by the arm pivot member 542 so that the upper end of the back lifting driven arm 54A is rotatable about the Y axis. The arm pivot member 542 supports the back bottom 101A via the back lifting driven arm 54A against the frame portion 20 from the side of the lower surface of the back bottom 101A.

The arm pivot member 542 may be integrally formed with the back bottom 101A and serve as a portion of the back bottom 101A. For example, the arm pivot member 542 may be achieved as a reinforcing member that is a portion of the back bottom 101A.

The electric motor 56A generates driving force to drive the back lifting arm 52A and rotate the back lifting arm 52A about the rotational pivot 521 and about the Y axis. The electric motor 56A is electrically connected to the power unit 60.

In the second embodiment, the sensor unit 90 is attached to the arm pivot member 542. In this case, the sensor unit 90 is attached to the arm pivot member 542 so that the sensing direction passes through the heart sensing-enabled region BT1. A position and angle at which the sensor unit 90 is attached to the arm pivot member 542 may be individually set based on the size of the body of the user 2 or the like.

A method for attaching the sensor unit 90 to the arm pivot member 542 is arbitrary. For example, the sensor unit 90 may be attached to the arm pivot member 542 using a fastener such as a bolt or a screw. Alternatively, the sensor unit 90 may be attached to the arm pivot member 542 using an adhesive, a tape, or the like. Alternatively, the sensor unit 90 may be attached directly to the arm pivot member 542 as schematically illustrated in FIG. 6 or may be attached to the arm pivot member 542 via a stay or a bracket as described later.

Figure 7:
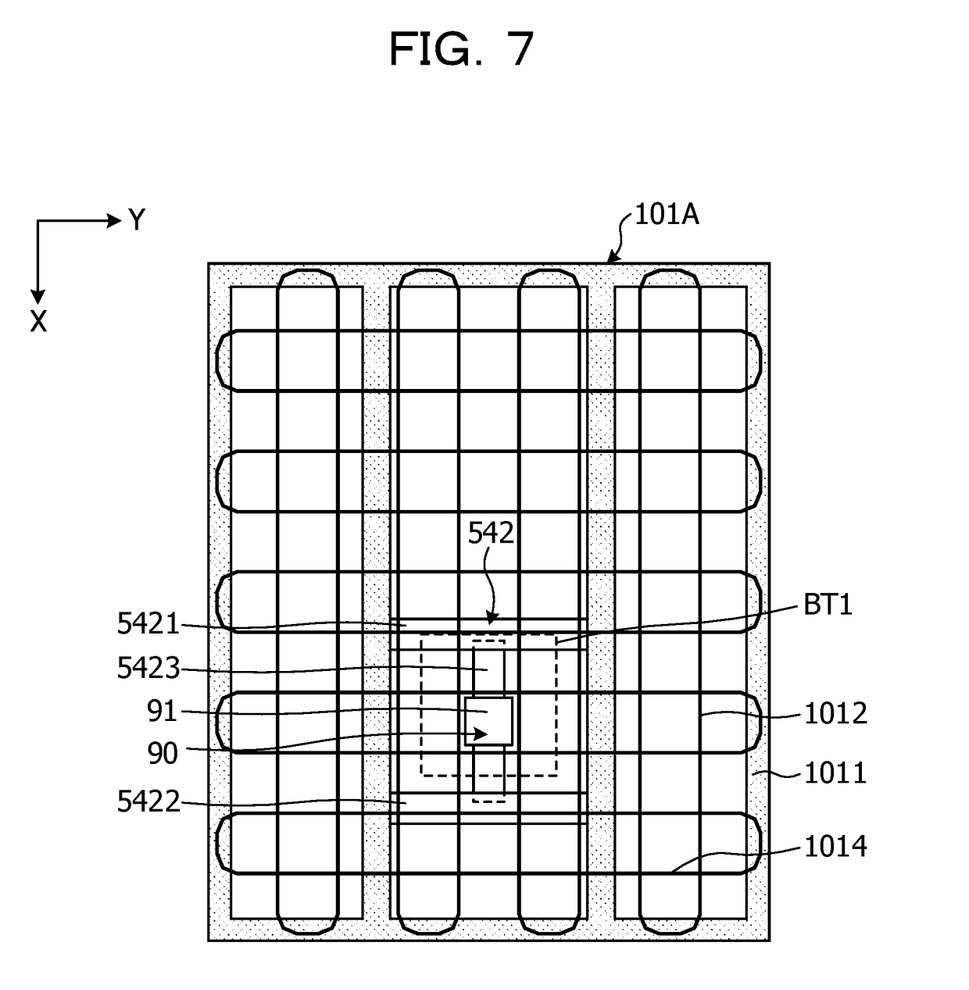
FIG. 7 is a diagram schematically illustrating an example of a state in which the sensor unit is attached when viewed in a direction indicated by an arrow Q2 in FIG. 6.

FIG. 7 is a diagram schematically illustrating an example of a state in which the sensor unit is attached when viewed in a direction indicated by an arrow Q2 in FIG. 6. The direction indicated by the arrow Q2 corresponds to a direction perpendicular to a flat surface of the back bottom 101A. FIG. 7 illustrates the back bottom 101A, the arm pivot member 542, and the sensor unit 90. In addition, FIG. 7 illustrates the heart sensing-enabled region BT1. In an example illustrated in FIG. 7, the heart sensing-enabled region BT1 is set to a central portion in the width direction (Y direction) of the bed 1.

In the example illustrated in FIG. 7, the back bottom 101A includes a body portion 1011, vertical mesh portions 1012, and vertical mesh portions 1014. The arm pivot member 542 is fixed on the side (side opposite to the side on which the back bottom 101A is in contact with the mattress 40) of the lower surface of the back bottom 101A. The arm pivot member 542 includes two horizontal frame portions 5421 and 5422 and a vertical frame portion 5423. The horizontal frame portions 5421 and 5422 extend in the Y direction, while there is a gap between the horizontal frame portions 5421 and 5422 in the X direction. The vertical frame portion 5423 extends in a central region that is located between the horizontal frame portions 5421 and 5422 in the Y direction. The vertical frame portion 5423 is fixed on the side of lower surfaces of the horizontal frame portions 5421 and 5422. In this case, a gap exists between the vertical frame portion 5423 and the back bottom 101A in the direction perpendicular to the flat surface of the back bottom 101A. In the example illustrated in FIG. 7, the sensor unit 90 is installed in the gap between the vertical frame portion 5423 and the back bottom 101A. For example, the sensor unit 90 is fixed to an upper surface of the vertical frame portion 5423.

In the example illustrated in FIG. 7, the sensor unit 90 is installed against the back bottom 101A so that the sensing direction corresponds to the direction perpendicular to the flat surface of the back bottom 101A. Thus, the sensing direction of the sensor unit 90 may pass through the heart sensing-enabled region BT1.

In the second embodiment, in the case where the bed 1 includes the back lifting mechanism 50A, a relative position of the body of the user 2 with respect to the mattress 40 may change depending on the back lifting angle. For example, if the posture of the user 2 is a supine state, a positional relationship between the mattress 40 and the body of the user 2 in the non-back-lifted state (refer to FIG. 1A) may be shifted from a positional relationship between the mattress 40 and the body of the user 2 in the back-lifted state (refer to FIG. 1B). This is due to the fact that the body of the user 2 is shifted with respect to the mattress 40 (especially, a portion located on the side of the lifted back) upon the transition from the non-back-lifted state to the back-lifted state. Thus, for example, in a comparative example in which the sensor unit 90 is installed in the mattress 40, it is difficult to maintain high detection accuracy depending on the back lifting angle.

On the other hand, in the second embodiment, as described above, the sensor unit 90 is not installed in the mattress 40 and is attached to the member fixed to the back bottom 101A or is attached to the arm pivot member 542. Thus, according to the second embodiment, the sensing direction of the sensor unit 90 toward the back bottom 101A does not change depending on the back lifting angle. In other words, according to the second embodiment, the sensing direction of the sensor unit 90 may pass through the heart sensing-enabled region BT1 regardless of the back lifting angle.

A position of the body of the user 2 with respect to the back bottom 101A hardly changes depending on the back lifting angle, differently from a relative position of the body of the user 2 with respect to the mattress 40. This is due to the fact that a direction which the body of the user 2 is shifted with respect to the mattress 40 upon the transition from the non-back-lifted state to the back-lifted state is opposite to a direction which the mattress 40 is shifted with respect to the back bottom 101A (or in which the mattress 40 slides down) upon the transition from the non-back-lifted state to the back-lifted state. Thus, according to the second embodiment, even in the non-back-lifted state and the back-lifted state, the state of the user 2 is likely to be accurately detected by the sensor unit 90.

In addition, in the second embodiment, since the sensor unit 90 is not installed in the mattress 40 and is attached to the arm pivot member 542, a load caused by an operation of the back lifting mechanism 50A is not applied to the sensor unit 90. It is, therefore, possible to suppress the detachment, caused by an operation of the back lifting mechanism 50A, of the sensor unit 90 and a positional shift, caused by an operation of the back lifting mechanism 50A, of the sensor unit 90. The sensor unit 90 is installed on the lower side of the back bottom 101A in the same manner as the aforementioned first embodiment. Thus, the sensor unit 90 is more reliably attached than the case where the sensor unit 90 is installed between the mattress 40 and the back bottom 101A.

In the second embodiment, the arm pivot member 542 is not a dedicated member to be used to attach the sensor unit 90 and may be an existing member. Thus, according to the first embodiment, the sensor unit 90 may be attached at an appropriate position while the number of members does not increase.

In the aforementioned second embodiment, the sensor unit 90 is attached to the arm pivot member 542 but is not limited to this. For example, the sensor unit 90 may be attached to a member (for example, the body portion 1011, a vertical mesh portion 1012, a vertical mesh portion 1014, or the like in the example illustrated in FIG. 7) forming a portion of the back bottom 101A. In this case, it is preferable that the sensor unit 90 be attached on the side of a lower surface of the member forming the portion of the back bottom 101A so that the sensor unit 90 is not in contact the mattress 40.

In the aforementioned second embodiment, the sensor unit 90 is attached directly to the existing member (member requested to maintain the strength and functions of the bed 1 for the structure of the bed 1) of the bed 1 but is not limited to this. For example, the sensor unit 90 may be attached to a dedicated member fixed to the back bottom 101A. The dedicated member is suitable for the case where a relative position of the arm pivot member 542 with respect to the back bottom 101A is separated from the heart sensing-enabled region BT1, for example. In this case, the dedicated member extends from the arm pivot member 542 toward the heart sensing-enabled region BT1.

In the aforementioned second embodiment, the sensor unit 90 is attached to the member (for example, the arm pivot member 542) fixed to the back bottom 101A but may be attached to a movable member that is displaced with respect to the back bottom 101A based on the back lifting angle. Specifically, the sensor unit 90 may be attached to the movable member of the back lifting mechanism 50A in the same manner as the aforementioned first embodiment. This is due to the fact that even if the movable member is displaced with respect to the back bottom 101A based on the back lifting angle, the sensing direction of the sensor unit 90 passes through the heart sensing-enabled region BT1 regardless of the back lifting angle, depending on the amount and direction of the displacement. In this case, if the sensor unit 90 is attached so that the sensor unit 90 is not in contact with the mattress 40, inconvenience caused by a shift (displacement) of the mattress 40 with respect to the back bottom 101A does not occur.

Although the embodiments are described above, the present disclosure is not limited to the specific embodiments, and the embodiments may be variously modified and changed within the scope of claims. In addition, all or two or more of the constituent elements described in the embodiments may be combined.

For example, in the aforementioned first embodiment (and the second embodiment), the bed 1 may have a mechanism for adjusting the height of the back portion 10.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A bed comprising:
   a frame installed horizontally with respect to a floor;
   a plate installed over the frame and having an end portion that is to be inclined upward with respect to the frame;
   an arm that supports the plate under a lower side of the end portion of the plate; and a sensor attached to the arm that is moveable on the plate as the plate is inclined upward so that an orientation of a sensing direction of the sensor with respect to the arm remains within a region of the plate while an angle of the plate with respect to the floor changes to detect a state of a user in the bed.

2. The bed according to claim 1, further comprising:
a mattress arranged over the plate installed over the frame.

3. The bed according to claim 2,
wherein in a state the plate is parallel to the frame, the sensing direction of the sensor is set to be oriented toward the mattress.

4. The bed according to claim 2,
wherein the region detected by the sensor is a central portion of the bed regardless of increasing of the angle of the plate with respect to the floor.

5. The bed according to claim 1,
wherein the sensor is a biological sensor.

6. The bed according to claim 1,
wherein the sensor emits a radio wave and acquires biological information based on a reflected wave of the radio wave.

7. The bed according to claim 1, further comprising:
an electric motor that drives the arm,
wherein the sensor is electrically connected to a power unit that supplies power to the electric motor.

8. The bed according to claim 1,
wherein the sensor is attached to the arm and located at a central portion in a width direction of the bed.

9. The bed according to claim 1,
wherein the arm includes two rollers that slidably support the plate and are separated from each other in a width direction of the bed, and
wherein the sensor is located between the two rollers in the width direction of the bed.

10. The bed according to claim 1,
wherein the sensor is attached to a surface included in the arm and arranged adjacent to the plate.

* * * * *